United States Patent
Fukui et al.

(10) Patent No.: US 7,557,061 B2
(45) Date of Patent: Jul. 7, 2009

(54) PROCESS FOR PRODUCING CATALYST FOR METHACRYLIC ACID SYNTHESIS

(75) Inventors: Tomoki Fukui, Otake (JP); Hiroyuki Naitou, Otake (JP); Tomomichi Hino, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 11/631,107

(22) PCT Filed: Jun. 24, 2005

(86) PCT No.: PCT/JP2005/011590

§ 371 (c)(1),
(2), (4) Date: Jan. 29, 2007

(87) PCT Pub. No.: WO2006/001360

PCT Pub. Date: Jan. 5, 2006

(65) Prior Publication Data

US 2007/0161819 A1    Jul. 12, 2007

(30) Foreign Application Priority Data

Jun. 28, 2004    (JP) .............................. 2004-189888

(51) Int. Cl.
  *B01J 27/19*      (2006.01)
  *C07C 51/16*      (2006.01)
(52) U.S. Cl. ...................... 502/211; 562/547
(58) Field of Classification Search ................. 562/547; 502/211
See application file for complete search history.

(56) References Cited

U.S. PATENT DOCUMENTS 4,596,784 A * 6/1986 Kennelly et al. ............ 502/209
5,681,790 A * 10/1997 Kim et al. ................... 502/164
2007/0032679 A1    2/2007 Naitou et al.

FOREIGN PATENT DOCUMENTS

| JP | 58 51943   | 3/1983 |
| JP | 58 112050  | 7/1983 |
| JP | 59 4445    | 1/1984 |
| JP | 4 182450   | 6/1992 |
| JP | 9 938      | 1/1997 |
| JP | 11 33403   | 2/1999 |

OTHER PUBLICATIONS

U.S. Appl. No. 11/631,107, filed Dec. 28, 2006, Fukui et al.

* cited by examiner

*Primary Examiner*—Taylor Victor Oh
(74) *Attorney, Agent, or Firm*—Oblon, Spivak, McClelland, Maier & Neustadt, P.C.

(57) ABSTRACT

The present invention provides a method for producing a catalyst for use in synthesizing methacrylic acid which can produce methacrylic acid in high yield, the catalyst for use in synthesizing methacrylic acid which can produce methacrylic acid in high yield and a method for producing methacrylic acid in high yield through gas-phase catalytic oxidation of methacrolein with molecular oxygen. The method for producing the catalyst containing molybdenum and phosphorus for use in synthesizing methacrylic acid is composed of the steps of: preparing a slurry containing at least molybdenum and phosphorus and having specific viscosity in the range of $2.5 \times 10^{-4}$ to $7.0 \times 10^{-4}$ m²/s, which is a value obtained by dividing viscosity (unit: kg/(m·s)) by specific gravity (unit: kg/m³); obtaining a dried material by drying the slurry; and calcining the dried material at 300 to 500° C.

17 Claims, No Drawings

PROCESS FOR PRODUCING CATALYST FOR METHACRYLIC ACID SYNTHESIS

TECHNICAL FIELD

The present invention relates to a method for producing a catalyst for use in synthesizing methacrylic acid, a catalyst for use in synthesizing methacrylic acid and a method for producing methacrylic acid through gas-phase catalytic oxidation of methacrolein with molecular oxygen.

BACKGROUND ART

It is publicly known that a heteropolyacid catalyst containing molybdenum and phosphorus is effective as a catalyst for use in synthesizing methacrylic acid through gas-phase catalytic oxidation of methacrolein. For example, a method for producing a catalyst for use in synthesizing methacrylic acid is proposed in Patent Document 1 wherein water content of a concentrated or dried material of a slurry obtained by mixing compounds containing catalyst-component elements is adjusted to 5 to 20% by mass followed by heat treatment at 100 to 250° C. A method for producing a catalyst for use in synthesizing methacrylic acid is proposed in Patent Document 2 wherein water content of a concentrated or dried material of a slurry obtained by mixing phosphomolybdic acid and compounds containing other catalyst-component elements is adjusted to 5 to 20% by mass followed by heat treatment at 100 to 300° C.

Patent Document 1: Japanese Patent Application Laid-Open No. Sho58-51,943
Patent Document 2: Japanese Patent Application Laid-Open No. Sho58-112,050

DISCLOSURE OF INVENTION

Problem to be Solves by the Invention

However, the catalysts produced by the methods described in Patent Documents 1 and 2 are industrially insufficient in point of yield of methacrylic acid, and hence further improvement in yield has been desired.

It is an object of the present invention to provide a method for producing a catalyst for use in synthesizing methacrylic acid which can produce methacrylic acid in high yield, the catalyst for use in synthesizing methacrylic acid which can produce methacrylic acid in high yield, and a method for producing methacrylic acid in high yield through gas-phase catalytic oxidation of methacrolein with molecular oxygen.

Means for Solving Problem

The first present invention is a method for producing a catalyst containing molybdenum and phosphorus for use in synthesizing methacrylic acid, comprising the steps of:

(a) preparing a slurry containing at least molybdenum and phosphorus and having specific viscosity in the range of $2.5 \times 10^{-4}$ to $7.0 \times 10^{-4}$ m$^2$/s, the specific viscosity being a value obtained by dividing viscosity (unit: kg/(m·s)) by specific gravity (unit: kg/m$^3$);

(b) obtaining a dried material by drying the slurry; and (c) calcining the dried material at 300 to 500° C.

Preferably, in the foregoing step (a), the slurry containing at least molybdenum and phosphorus and having specific viscosity which is lower than a target specific viscosity is concentrated to the point where the target specific viscosity is obtained.

The second present invention is a catalyst containing molybdenum and phosphorus for use in synthesizing methacrylic acid, produced by the method of the first invention.

The third present invention is a method for producing methacrylic acid through gas-phase catalytic oxidation of methacrolein with molecular oxygen by using the catalyst containing molybdenum and phosphorus for use in synthesizing methacrylic acid of the second invention.

Effects of the Invention

According to the first present invention, a catalyst for use in synthesizing methacrylic acid which can produce methacrylic acid in high yield can be produced.

By using the catalyst for use in synthesizing methacrylic acid of the second present invention, methacrylic acid can be produced in high yield.

According to the method for producing methacrylic acid of the third present invention, methacrylic acid can be produced in high yield through gas-phase catalytic oxidation of methacrolein with molecular oxygen.

BEST MODE FOR CARRYING OUT THE INVENTION

The catalyst for use in synthesizing methacrylic acid which is produced by the method of the present invention (hereinafter, also merely expressed as catalyst) is a composite oxide containing at least molybdenum and phosphorus. The composite oxide preferably contains a structure of heteropolyacid and/or heteropolyacid salt. The fact that the catalyst is the composite oxide and contains the structure of heteropolyacid and/or heteropolyacid salt can be confirmed with XRD.

Further, the catalyst preferably contains an alkaline metal besides molybdenum and phosphorus, and may contain, in addition to these elements, copper, vanadium, iron, cobalt, nickel, zinc, magnesium, calcium, strontium, barium, titan, chromium, tungsten, manganese, silver, boron, silicon, aluminum, gallium, germanium, tin, lead, arsenic, antimony, bismuth, niobium, tantalum, zirconium, indium, sulfur, selenium, tellurium, lanthanum, cerium, or the like. The catalyst is preferably the composite oxide represented by the following compositional formula (1).

$$Mo_aP_bCu_cV_dX_eY_fO_g \qquad (1)$$

In the formula (1), Mo, P, Cu, V and O represent molybdenum, phosphorus, copper, vanadium, and oxygen, respectively; X represents at least one element selected from the group consisting of potassium, rubidium, cesium, and thallium; Y represents at least one element selected from the group consisting of iron, cobalt, nickel, zinc, magnesium, calcium, strontium, barium, titan, chromium, tungsten, manganese, silver, boron, silicon, aluminum, gallium, germanium, tin, lead, arsenic, antimony, bismuth, niobium, tantalum, zirconium, indium, sulfur, selenium, tellurium, lanthanum, and cerium; a, b, c, d, e, f, and g represent atomic ratios of respective elements; when a is 12, b is in the range of from 0.1 to 3, c is in the range of from 0.01 to 3, d is in the range of from 0.01 to 3, e is in the range of from 0.01 to 3, f is in the range of from 0 to 3, and g represents the atomic ratio of oxygen necessary for fulfilling the requirement of the atomic ratio of each component above.

In the method for producing the catalyst of the present invention, a slurry containing at least molybdenum and phosphorus and having specific viscosity in the range of $2.5 \times 10^{-4}$ to $7.0 \times 10^{-4}$ m$^2$/s, which is a value obtained by dividing viscosity (unit: kg/(m·s)) by specific gravity (unit: kg/m$^3$) (hereinafter, also merely expressed as slurry), is prepared (step (a)); the slurry is dried (step (b)); and the dried material thus obtained is calcined at 300 to 500° C. (step (c)).

The slurry containing at least molybdenum and phosphorus and having the specified specific viscosity mentioned above can be prepared, using raw materials of respective component elements of the catalyst (hereinafter, expressed as catalyst raw materials), with conventional coprecipitation method, oxide mixing method, or the like. The catalyst raw materials to be used in the preparation of the slurry are not particularly limited and nitrates, carbonates, acetates, ammonium salts, oxides, halides, oxoacids, and oxoacid salts of respective component elements of the catalyst can be used in combination. As the raw material of molybdenum, for example, ammonium paramolybdate, molybdenum trioxide, molybdic acid, and molybdenum chloride can be used. As the raw material of phosphorus, for example, phosphoric acid, phosphorus pentoxide, and ammonium phosphate can be used. As the solvent, for example, water, ethyl alcohol, and acetone can be listed and water is preferably used.

As the preferable procedure for preparing the slurry, for example, a method of suspending in water the raw material of molybdenum such as a molybdenum oxide or ammonium paramolybdate followed by mixing the other catalyst raw materials with the suspension thus obtained is listed. The other catalyst raw materials can be used as they are or by properly dissolving or suspending them in liquid media such as water. Further, aqueous ammonia may be added in the course of mixing the catalyst raw materials or after the mixing.

The foregoing slurry having the specified specific viscosity, for example, can be produced by concentrating the slurry having specific viscosity which is lower than the target specific viscosity. Concentration means the operation of heating the slurry and vaporizing the solvent in the slurry. The concentration, for example, can be carried out by heating a vessel such as a reaction vessel containing the slurry using heat source such as electric heater or steam. The temperature of the slurry at the time of the concentration is not particularly limited, however, it is preferably 50° C. to 110° C., more preferably 90° C. to 108° C., furthermore preferably 95° C. to 105° C. The viscosity and the specific gravity of the slurry during the concentration are properly measured by sampling the slurry, and the concentration is finished when the specific viscosity reaches the target specific viscosity in the range of $2.5 \times 10^{-4}$ to $7.0 \times 10^{-4}$ m$^2$/s, preferably in the range of $3.0 \times 10^{-4}$ to $6.5 \times 10^{-4}$ m$^2$/s. Specific viscosity is a value calculated by dividing the viscosity (unit: kg/(m·s)) by the specific gravity (unit: kg/m$^3$). Viscosity is measured by sampling a portion of the slurry and using B type viscometer. The measurement of the viscosity is preferably carried out after the slurry is stirred. Specific gravity is calculated by sampling a portion of the slurry, measuring its mass and its volume and dividing the mass by the volume. Measurements of the viscosity and the specific gravity of the slurry during its concentration may be carried out either continuously or intermittently, however, it is preferable to carry out intermittently at intervals of within 5 minutes.

"Concentration is finished" means that vaporization of water is suppressed as far as possible by a method of, for example, stopping heating. Concretely, it is preferable to stop heating and put the lid on the reaction vessel.

In the present invention, the prepared slurry having the specified specific viscosity can be dried immediately, however, it can also be stored in the state of slurry before dried. When the slurry is stored, the specific viscosity of the slurry is kept in the range of $2.5 \times 10^{-4}$ to $7.0 \times 10^{-4}$ m$^2$/s, preferably in the range of $3.0 \times 10^{-4}$ to $6.5 \times 10^{-4}$ m$^2$/s. The storage time of the slurry is not particularly limited as long as the specific viscosity of the slurry is within the foregoing range. However, the storage time is preferably 30 days or less, more preferably 5 days or less, because the productivity of the catalyst becomes higher as the storage time becomes shorter.

In the present invention, the slurry having the specific viscosity in the range of $2.5 \times 10^{-4}$ to $7.0 \times 10^{-4}$ m$^2$/s is dried (step (b)). For drying, a device that can dry the slurry in a short time such as spray dryer, drum dryer and slurry dryer can be used. The temperature at the time of drying is not particularly limited, however, it is preferably 120° C. to 500° C., more preferably 130° C. to 400° C., furthermore preferably 140° C. to 350° C. The drying time is not particularly limited, however, it is preferably 0.1 second to 10 minutes, more preferably 0.3 second to 5 minutes. Drying is preferably carried out to the extent that the water content of the dried material to be obtained becomes less than 3% by mass. Water content of the dried material can be measured with Kett Moisture Tester by sampling a portion of it.

Subsequently, the dried material thus obtained is calcined at 300 to 500° C., preferably at 300 to 450° C. The calcination is ordinarily carried out under the flow of oxygen-containing gas such as air and/or under the flow of inert gas. The calcination time is ordinarily 0.5 hour or more, preferably 1 to 40 hours.

When the molded catalyst is produced, the calcined material obtained by calcining the dried material without modification may be molded, however, it is preferable to previously mold the dried material and then calcine the molded article thus obtained. The method of molding is not particularly limited and various molding methods such as tablet molding, extrusion molding and granulation can be used. When molding is carried out, additives or filling materials such as inorganic salts which include barium sulfate and ammonium sulfate; lubricants which include graphite; organic materials which include cellulose, starch, polyvinyl alcohol, and stearic acid; hydroxyl sols which include silica sol and alumina sol; and inorganic fibers which include whisker, glass fiber, and carbon fiber may be properly added with the view of producing molded articles having a uniform specific surface area, pore volume, and pore distribution in good reproducibility, improving mechanical strength of the molded articles, or the like. The shape of the molded article is not particularly limited and spherical shape, cylindrical shape, ring shape or plate shape can be listed.

The reason why the catalyst that can produce methacrylic acid in high yield can be produced by carrying out the above-mentioned procedure is not clear, however, it is presumed that an intermediate of the crystal structure which functions advantageously in gas-phase catalytic oxidation reaction of methacrolein be formed when the specific viscosity of the slurry is in the foregoing specified range.

Next, the method for producing methacrylic acid through gas-phase catalytic oxidation of methacrolein with molecular oxygen by using the catalyst of the present invention thus obtained will be explained.

In the gas-phase catalytic oxidation (hereinafter, also merely expressed as reaction), the raw gas containing at least methacrolein and molecular oxygen is contacted with the catalyst. Ordinarily, a tubular reactor filled with the catalyst is used for the reaction. Industrially, a multitubular reactor is used.

Concentration of methacrolein in the raw gas to be used in the reaction can be set in a wide range, however, it is preferably 1 to 20% by volume, particularly preferably 3 to 10% by volume. The raw methacrolein sometimes contains a small amount of impurities such as water, lower saturated aldehydes, and the like which do not substantially affect the reaction, and the raw gas may also contain those impurities originating from methacrolein.

The amount of molecular oxygen in the raw gas is preferably 0.4 to 4 times by mole as much as that of methacrolein, particularly preferably 0.5 to 3 times by mole. As a source of molecular oxygen in the raw gas, using air is industrially advantageous, however if necessary, pure oxygen-enriched air can be used. Further, the raw gas is preferably diluted with an inert gas such as nitrogen or carbon dioxide, steam, or the like.

The reaction pressure is preferably from atmospheric pressure to 5 atm, more preferably from atmospheric pressure to 3 atm. The reaction temperature is preferably 200 to 450° C., more preferably 250 to 400° C. The contact time of the raw gas with the catalyst is preferably 1.5 to 15 seconds, more preferably 2 to 7 seconds.

EXAMPLES

Hereinafter, the present invention will be explained with reference to Examples and Comparative Examples. The term "part(s)" in the Examples and Comparative Examples means part(s) by mass. Quantitative analysis of the raw gas and the products were carried out with gas chromatography. Conversion of the raw methacrolein, selectivity to and per pass yield of the product methacrylic acid are defined as follows:

Conversion of methacrolein (%)=($B/A$)×100;

Selectivity to methacrylic acid (%)=($C/B$)×100; and

Per pass yield of methacrylic acid (%)=($C/A$)×100.

In these formulae, A represents mole number of methacrolein supplied, B represents mole number of methacrolein reacted and C represents mole number of methacrylic acid produced.

In the Examples and Comparative Examples, viscosity (kg/(m·s)) of the slurry was measured by B type viscometer after sampling a portion of the slurry, and sufficiently stirring the sample not to segregate the solids constituent. Specific gravity (kg/m$^3$) of the slurry was calculated by sampling a portion of the slurry, measuring its volume (m$^3$) and its mass (kg) and dividing the mass by the volume. During concentration of the slurry, these measurement were carried out at intervals of 5 minutes. Specific viscosity (m$^2$/s) was calculated by dividing the viscosity (kg/(m·s)) by the specific gravity (kg/m$^3$). Water content of the dried material was measured with Kett Moisture Tester.

The fact that the catalyst is a composite oxide and contains the structure of heteropolyacid and/or its salt was confirmed with XRD.

Example 1

To 400 parts of pure water, 100 parts of molybdenum trioxide, 7.3 parts of 85% by mass aqueous phosphoric acid, 4.2 parts of vanadium pentoxide, 0.9 part of copper oxide, and 0.2 part of iron oxide were added and stirred under reflux condition for 5 hours. The resultant liquid was cooled to 50° C. and 37.4 parts of 29% by mass aqueous ammonia was dropped to it and stirred for 15 minutes. Subsequently, a solution obtained by dissolving 9.0 parts of cesium nitrate in 30 parts of pure water was dropped to it and stirred for 15 minutes to obtain a slurry.

The slurry was heated to 101° C. and the concentration was started while it was stirred. At the beginning of the concentration, the viscosity of the slurry was 0.03 kg/(m·s), the specific gravity was 1.25×10$^3$ kg/m$^3$, and the specific viscosity was 2.4×10$^{-5}$ m$^2$/s. The temperature was kept at 101° C. during the concentration, and heating was stopped and the concentration was finished when the viscosity of the slurry was 0.70 kg/(m·s), the specific gravity was 1.56×10$^3$ kg/m$^3$, and the specific viscosity was 4.5×10$^{-4}$ m$^2$/s. The time spent for the concentration was 2 hours.

The slurry right after the concentration was dried with a spray dryer at the inlet temperature of 300° C. and the outlet temperature of 1 20° C. The water content of the dried material thus obtained was 0.9% by mass. To 100 parts of the dried material, 2 parts of graphite was added and the mixture thus obtained was molded to ring shape having an outer diameter of 5 mm, an inner diameter of 2 mm, and a length of 5 mm with a tablet molding machine. The molded articles thus obtained were calcined at 375° C. for 10 hours under air flow and a composite oxide catalyst having the composition of Mo$_{12}$P$_{1.1}$Cu$_{0.2}$V$_{0.8}$Cs$_{0.8}$Fe$_{0.05}$ (oxygen and its atomic ratio were abbreviated, and the same hereinafter) and containing the structure of heteropolyacid and its salt was obtained.

The catalyst was filled in a reactor and mixed gas composed of 5% of methacrolein, 10% of oxygen, 30% of water vapor, and 55% of nitrogen (volume %) was passed through it with the reaction pressure of 1013 hPa (pressure at the exit of the reactor), the reaction temperature of 285° C., and the contact time of 3.6 seconds to carry out the reaction for synthesizing methacrylic acid. The result is shown in Table 1.

Example 2

The same procedure as in Example 1 was carried out except that the concentration was finished when the viscosity of the slurry was 0.53 kg/(m·s), the specific gravity was 1.52×10$^3$ kg/m$^3$, and the specific viscosity was 3.5×10$^{-4}$ m$^2$/s, to produce the catalyst of the same composition and to synthesize methacrylic acid. The result is shown in Table 1.

Example 3

The same procedure as in Example 1 was carried out except that the concentration was finished when the viscosity of the slurry was 0.88 kg/(m·s), the specific gravity was 1.60×10$^3$ kg/m$^3$, and the specific viscosity was 5.5×10$^{-4}$ m$^2$/s, to produce the catalyst of the same composition and to synthesize methacrylic acid. The result is shown in Table 1.

Comparative Example 1

The same procedure as in Example 1 was carried out except that the concentration was finished when the viscosity of the slurry was 1.30 kg/(m·s), the specific gravity was 1.63×10$^3$ kg/m$^3$, and the specific viscosity was 8.0×10$^{-4}$ m$^2$/s, to produce the catalyst of the same composition and to synthesize methacrylic acid. The result is shown in Table 1.

Comparative Example 2

The same procedure as in Example 1 was carried out except that the concentration was finished when the viscosity of the slurry was 1.50 kg/(m·s), the specific gravity was 1.67×10$^3$ kg/m$^3$, and the specific viscosity was 9.0×10$^{-4}$ m$^2$/s, to produce the catalyst of the same composition and to synthesize methacrylic acid. The result is shown in Table 1.

Comparative Example 3

The same procedure as in Example 1 was carried out except that the concentration was finished when the viscosity of the slurry was 0.27 kg/(m·s), the specific gravity was $1.35 \times 10^3$ kg/m$^3$, and the specific viscosity was $2.0 \times 10^{-4}$ m$^2$/s, to produce the catalyst of the same composition and to synthesize methacrylic acid. The result is shown in Table 1.

Comparative Example 4

The same procedure as in Example 1 was carried out except that the concentration was finished when the viscosity of the slurry was 0.10 kg/(m·s), the specific gravity was $1.25 \times 10^3$ kg/m$^3$, and the specific viscosity was $8.0 \times 10^{-5}$ m$^2$/s, to produce the catalyst of the same composition and to synthesize methacrylic acid. The result is shown in Table 1.

Example 4

In 200 parts of pure water, 100 parts of ammonium paramolybdate was dissolved, and to the resultant solution, 3.4 parts of ammonium methavanadate, a solution obtained by dissolving 8.2 parts of 85% by mass aqueous phosphoric acid in 30 parts of pure water, a solution obtained by dissolving 1.1 parts of copper nitrate in 30 parts of pure water, and a solution obtained by dissolving 3.8 parts of iron nitrate in 10 parts of pure water were added in this order, and the resultant liquid was heated to 90° C. while stirred, and kept at 90° C. while stirred for 5 hours. To the resultant liquid, a solution obtained by dissolving 9.2 parts of cesium nitrate in 100 parts of pure water was added and stirred for 15 minutes to obtain a slurry.

The slurry was heated to 101° C. and the concentration was started while it was stirred. At the beginning of the concentration, the viscosity of the slurry was 0.02 kg/(m·s), the specific gravity was $1.22 \times 10^3$ kg/m$^3$, and the specific viscosity was $1.6 \times 10^{-5}$ m$^2$/s. The temperature was kept at 101° C. during the concentration, and heating was stopped and the concentration was finished when the viscosity of the slurry was 0.68 kg/(m·s), the specific gravity was $1.58 \times 10^3$ kg/m$^3$ and the specific viscosity was $4.3 \times 10^{-4}$ m$^2$/s. The time spent for the concentration was 2.5 hours.

The slurry right after the concentration was dried with a drum dryer at the temperature of 300° C. The water content of the dried material thus obtained was 1.0% by mass. To 100 parts of the dried material, 2 parts of graphite was added and the mixture thus obtained was molded to ring shape having an outer diameter of 5 mm, an inner diameter of 2 mm, and a length of 5 mm with a tablet molding machine. The molded articles thus obtained were calcined at 380° C. for 6 hours under air flow and a composite oxide catalyst having the composition of $Mo_{12}P_{1.5}Cu_{0.1}V_{0.6}Cs_1Fe_{0.2}$ and containing the structure of heteropolyacid and its salt was obtained.

The catalyst was filled in a reactor and mixed gas composed of 5% of methacrolein, 10% of oxygen, 30% of water vapor, and 55% of nitrogen (volume %) was passed through it with the reaction pressure of 1013 hPa (pressure at the exit of the reactor), the reaction temperature of 285° C., and the contact time of 3.6 seconds to carry out the reaction for synthesizing methacrylic acid. The result is shown in Table 1.

Example 5

The same procedure as in Example 4 was carried out except that the concentration was finished when the viscosity of the slurry was 0.85 kg/(m·s), the specific gravity was $1.60 \times 10^3$ kg/m$^3$, and the specific viscosity was $5.3 \times 10^{-4}$ m$^2$/s, to produce the catalyst of the same composition and to synthesize methacrylic acid. The result is shown in Table 1.

Comparative Example 5

The same procedure as in Example 4 was carried out except that the concentration was finished when the viscosity of the slurry was 0.26 kg/(m·s), the specific gravity was $1.37 \times 10^3$ kg/$^3$, and the specific viscosity was $1.9 \times 10^{-4}$ m$^2$/s, to produce the catalyst of the same composition and to synthesize methacrylic acid. The result is shown in Table 1.

Comparative Example 6

The same procedure as in Example 4 was carried out except that the concentration was finished when the viscosity of the slurry was 1.30 kg/(m·s), the specific gravity was $1.65 \times 10^3$ kg/m$^3$, and the specific viscosity was $7.9 \times 10^{-4}$ m$^2$/s, to produce the catalyst of the same composition and to synthesize methacrylic acid. The result is shown in Table 1.

Example 6

To 800 parts of pure water, 100 parts of molybdenum trioxide, 3.1 parts of vanadium pentoxide, and 6.7 parts of 85% by mass aqueous phosphoric acid were added and stirred under reflux condition for 6 hours. To the liquid thus obtained, 2.4 parts of copper acetate was added and further stirred under reflux condition for 3 hours. The resultant liquid was cooled to 40° C. and a solution obtained by dissolving 11.2 parts of cesium bicarbonate in 100 parts of pure water was dropped to it and a solution obtained by dissolving 5.6 parts of ammonium carbonate in 100 parts of pure water was further dropped to it at 40° C. and stirred for 15 minutes to obtain a slurry.

The slurry was heated to 101° C. and the concentration was started while it was stirred. At the beginning of the concentration, the viscosity of the slurry was 0.02 kg/(m·s), the specific gravity was $1.11 \times 10^3$ kg/m$^3$, and the specific viscosity was $1.8 \times 10^{-5}$ m$^2$/s. The temperature was kept at 101° C. during the concentration, and heating was stopped and the concentration was finished when the viscosity of the slurry was 0.59 kg/(m·s), the specific gravity was $1.31 \times 10^3$ kg/m$^3$, and the specific viscosity was $4.5 \times 10^4$ m$^2$/s. The time spent for the concentration was 2.3 hours.

The slurry right after the concentration was dried with a spray dryer at the inlet temperature of 300° C. and the outlet temperature of 120° C. The water content of the dried material thus obtained was 0.8% by mass. To 100 parts of the dried material, 2 parts of graphite was added and the mixture thus obtained was molded to ring shape having an outer diameter of 5 mm, an inner diameter of 2 mm, and a length of 5 mm with a tablet molding machine. The molded articles thus obtained were calcined at 380° C. for 5 hours under air flow and a composite oxide catalyst having the composition of $Mo_{12}P_1Cu_{0.2}V_{0.6}Cs_1$ and containing the structure of heteropolyacid and its salt was obtained.

The catalyst was filled in a reactor and mixed gas composed of 5% of methacrolein, 10% of oxygen, 30% of water vapor, and 55% of nitrogen (volume %) was passed through it with the reaction pressure of 1013 hPa (pressure at the exit of the reactor), the reaction temperature of 285° C., and the contact time of 3.6 seconds to carry out the reaction for synthesizing methacrylic acid. The result is shown in Table 1.

Example 7

The same procedure as in Example 6 was carried out except that the concentration was finished when the viscosity of the slurry was 0.80 kg/(m·s), the specific gravity was 1.33×10³ kg/m³, and the specific viscosity was 6.0×10⁻⁴ m²/s, to produce the catalyst of the same composition and to synthesize methacrylic acid. The result is shown in Table 1.

Comparative Example 7

The same procedure as in Example 6 was carried out except that the concentration was finished when the viscosity of the slurry was 0.25 kg/(m·s), the specific gravity was 1.25×10³ kg/m³, and the specific viscosity was 2.0×10⁻⁴ m²/s, to produce the catalyst of the same composition and to synthesize methacrylic acid. The result is shown in Table 1.

Comparative Example 8

The same procedure as in Example 6 was carried out except that the concentration was finished when the viscosity of the slurry was 1.30 kg/(m·s), the specific gravity was 1.41×10³ kg/m³, and the specific viscosity was 9.2×10⁻⁴ m²/s, to produce the catalyst of the same composition and to synthesize methacrylic acid. The result is shown in Table 1.

TABLE 1

| | Specific viscosity of the slurry at the time of finishing the concentration (m²/s) | Conversion of methacrolein (%) | Selectivity to methacrylic acid (%) | Per pass yield of methacrylic acid (%) |
|---|---|---|---|---|
| Example 1 | 4.5 × 10⁻⁴ | 84.2 | 84.9 | 71.5 |
| Example 2 | 3.5 × 10⁻⁴ | 84.6 | 84.2 | 71.2 |
| Example 3 | 5.5 × 10⁻⁴ | 84.2 | 84.6 | 71.2 |
| Comp. Ex. 1 | 8.0 × 10⁻⁴ | 83.5 | 82.4 | 68.8 |
| Comp. Ex. 2 | 9.0 × 10⁻⁴ | 82.1 | 83.2 | 68.3 |
| Comp. Ex. 3 | 2.0 × 10⁻⁴ | 84.1 | 81.5 | 68.5 |
| Comp. Ex. 4 | 8.0 × 10⁻⁵ | 83.9 | 81.2 | 68.1 |
| Example 4 | 4.3 × 10⁻⁴ | 83.2 | 84.3 | 70.1 |
| Example 5 | 5.3 × 10⁻⁴ | 83.3 | 83.8 | 69.8 |
| Comp. Ex. 5 | 1.9 × 10⁻⁴ | 82.6 | 81.2 | 67.1 |
| Comp. Ex. 6 | 7.9 × 10⁻⁴ | 82.5 | 81.5 | 67.2 |
| Example 6 | 4.5 × 10⁻⁴ | 86.2 | 84.8 | 73.1 |
| Example 7 | 6.0 × 10⁻⁴ | 86.1 | 84.7 | 72.9 |
| Comp. Ex. 7 | 2.0 × 10⁻⁴ | 85.8 | 83.9 | 72.0 |
| Comp. Ex. 8 | 9.2 × 10⁻⁴ | 85.6 | 83.8 | 71.7 |

What is claimed is:

1. A method for producing a catalyst comprising molybdenum and phosphorus, said method comprising:
   (a) preparing a slurry comprising at least molybdenum and phosphorus and having specific viscosity in the range of 2.5×10⁻⁴ to 7.0×10⁻⁴ m²/s, the specific viscosity being a value obtained by dividing viscosity having a unit of kg/(m·s) by specific gravity having a unit of kg/m³;
   (b) obtaining a dried material by drying the slurry using a device selected from spray dryer, drum dryer and slurry dryer; and
   (c) calcining the dried material at 300 to 500° C.;
   wherein said catalyst is suitable for synthesizing methacrylic acid.

2. The method of claim 1, wherein, in the step (a), the slurry having said specific viscosity which is lower then a target specific viscosity is concentrated to the point where the target specific viscosity is obtained.

3. A method for producing methacrylic acid, comprising: gas-phase catalytic oxidation of methacrolein with molecular oxygen by using the catalyst of claim 1.

4. A method for producing methacrylic acid, comprising: gas-phase catalytic oxidation of methacrolein with molecular oxygen by using the catalyst of claim 1.

5. The method of claim 1, wherein said catalyst is a composite oxide comprising at least molybdenum and phosphorus.

6. The method of claim 1, wherein said catalyst comprises a structure of heteropolyacid and/or heteropolyacid salt.

7. The method of claim 1, wherein said catalyst is a composite oxide represented by the following formula (1):

$$Mo_aP_bCu_cV_dX_eY_fO_g \qquad (1),$$

wherein

Mo, P, Cu, V and O represent molybdenum, phosphorus, copper, vanadium, and oxygen, respectively;

X represents at least one element selected from the group consisting of potassium, rubidium, cesium, and thallium;

Y represents at least one element selected from the group consisting of iron, cobalt, nickel, zinc, magnesium, calcium, strontium, barium, titan, chromium, tungsten, manganese, silver, boron, silicon, aluminum, gallium, germanium, tin, lead, arsenic, antimony, bismuth, niobium, tantalum, zirconium, indium, sulfur, selenium, tellurium, lanthanum, and cerium;

a, b, c, d, e, f, and g represent atomic ratios of respective elements; when a is 12, b is in the range of from 0.1 to 3, c is in the range of from 0.01 to 3, d is in the range of from 0.01 to 3, e is in the range of from 0.01 to 3, f is in the range of from 0 to 3, and g represents the atomic ratio of oxygen necessary for fulfilling the requirement of the atomic ratio of each component above.

8. The method of claim 1, wherein said slurry is dried at a temperature of 120° C. to 500° C.

9. The method of claim 1, wherein said slurry is dried for 0.1 seconds to 10 minutes.

10. The method of claim 1, wherein said slurry is dried to an extent that a water content of the dried material is less than 3% by mass.

11. The method of claim 1, wherein said calcination is carried out under the flow of oxygen-containing gas and/or under the flow of inert gas.

12. The method of claim 1, wherein a calcination time is 0.5 hours or more.

13. The method of claim 1, wherein said slurry is concentrated in step a) by heating the slurry and vaporizing a solvent in the slurry.

14. The method of claim 1, wherein said slurry is concentrated in step a) at a temperature of 50° C. to 110° C.

15. The method of claim 1, wherein said slurry comprises water.

16. A method for producing a catalyst comprising molybdenum and phosphorus, said method comprising:
   (a) preparing a slurry comprising at least molybdenum and phosphorus and having specific viscosity in the range of 2.5×10⁻⁴ to 7.0×10⁻⁴ m²/s, the specific viscosity being a value obtained by dividing viscosity having a unit of kg/(m·s) by specific gravity having a unit of kg/m³;
   (b) obtaining a dried material by drying the slurry; and
   (c) calcining the dried material at 300 to 500° C.;

wherein said catalyst comprises a structure of heteropolyacid and/or heteropolyacid salt; and wherein said catalyst is suitable for synthesizing methacrylic acid.

17. A method for producing a catalyst comprising molybdenum and phosphorus, said method comprising:
  (a) preparing a slurry comprising at least molybdenum and phosphorus and having specific viscosity in the range of $2.5 \times 10^{-4}$ to $7.0 \times 10^{-4}$ m$^2$/s, the specific viscosity being a value obtained by dividing viscosity having a unit of kg/(m·s) by specific gravity having a unit of kg/m$^3$;
  (b) obtaining a dried material by drying the slurry; and
  (c) calcining the dried material at 300 to 500° C.;

wherein said catalyst comprises a structure of heteropolyacid and/or heteropolyacid salt; and wherein said catalyst is suitable for synthesizing methacrylic acid.

\* \* \* \* \*